(12) United States Patent
Dutzmann et al.

(10) Patent No.: US 6,620,822 B1
(45) Date of Patent: Sep. 16, 2003

(54) FUNGICIDAL COMBINATIONS OF ACTIVE SUBSTANCE

(75) Inventors: Stefan Dutzmann, Langenfeld (DE); Klaus Stenzel, Düssseldorf (DE); Astrid Mauler-Machnik, Leichlingen (DE); Ulrike Wachendorff-Neumann, Neuwied (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/031,175

(22) PCT Filed: Jul. 7, 2000

(86) PCT No.: PCT/EP00/06470
§ 371 (c)(1),
(2), (4) Date: Jan. 16, 2002

(87) PCT Pub. No.: WO01/05228
PCT Pub. Date: Jan. 25, 2001

(30) Foreign Application Priority Data

Jul. 20, 1999 (DE) .......................... 199 33 938

(51) Int. Cl.$^7$ .................... A61K 31/44; A61K 31/555; A61K 31/535; A61K 31/47; A01N 55/02

(52) U.S. Cl. .................... 514/299; 514/184; 514/229.2; 514/309

(58) Field of Search .................... 514/184, 229.2, 514/299, 309

(56) References Cited

U.S. PATENT DOCUMENTS

| | | | |
|---|---|---|---|
| 3,952,002 A | 4/1976 | Kramer et al. | 260/380 R |
| 5,059,623 A | 10/1991 | Krüger et al. | 514/613 |
| 5,240,940 A | 8/1993 | Arnold et al. | 514/312 |
| 5,453,531 A | 9/1995 | Seitz et al. | 560/29 |
| 5,789,430 A | 8/1998 | Jautelat et al. | 514/272.4 |
| 6,075,030 A | 6/2000 | Wagner et al. | 514/275 |
| 6,080,749 A | 6/2000 | Wagner et al. | 514/269 |
| 6,172,083 B1 | 1/2001 | Wagner et al. | 514/311 |
| 6,177,446 B1 | 1/2001 | Wagner et al. | 514/311 |

FOREIGN PATENT DOCUMENTS

| | | |
|---|---|---|
| DE | 41 39 637 | 6/1993 |
| DE | 19939841 | * 5/2000 |
| EP | 0 106 105 | 4/1984 |
| EP | 0 106 106 | 4/1984 |
| EP | 0 326 330 | 8/1989 |
| EP | 0 910 948 | 10/2001 |
| WO | 98/51146 | 11/1998 |
| WO | 98/54146 | 12/1998 |

OTHER PUBLICATIONS

Weeds, 15 1967, S.R. Colby, "Calculating Synergistic and Antagonistic Responses of Herbicide Combinations".
*D.W. Hollomon et al: Defining the resistance risk of the new powdery mildew funicide Quinoxyfen, Pesticide Science, GB, Elsevier Applied Science P blisher, Barking, Bd. 51, 1997, Selten 347–351, XP002096857 ISSN: 0031–613X Seite 347, die Zusammenfassung Seite 348, Absatz 1–Absatz 2; Tabellen 1,2 Seite 351, letzter Absatz.

* cited by examiner

Primary Examiner—Alton Pryor
(74) Attorney, Agent, or Firm—Richard E. L. Henderson; John E. Mrozinski, Jr.

(57) ABSTRACT

The novel active compound combinations of 5,7-dichloro-4-(4-fluoro-phenoxy)-quinoline of the formula

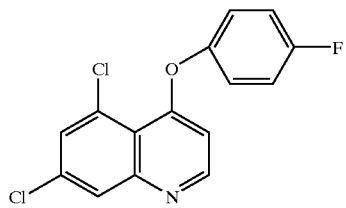

(I)

and the active compounds of groups (1) to (8) listed in the description have very good fungicidal properties.

5 Claims, No Drawings

FUNGICIDAL COMBINATIONS OF ACTIVE SUBSTANCE

FIELD OF THE INVENTION

The present invention relates to novel active compound combinations which comprise the known 5,7-dichloro-4-(4-fluoro-phenoxy)-quinoline on the one hand and other known fungicidally active compounds on the other hand, and which are highly suitable for controlling phytopathogenic fungi.

BACKGROUND OF THE INVENTION

It is already known that 5,7-dichloro-4-(4-fluoro-phenoxy)-quinoline has fungicidal properties (cf. EP-A 0 326 330). The activity of this substance is good; however, at low application rates it is in some cases unsatisfactory.

Furthermore, it is already known that certain combinations of 5,7-dichloro-4-(4-fluoro-phenoxy)-quinoline with other known fungicidally active compounds can be employed for controlling fungi (cf. EP-A 0 326 330, WO 96/18 299 and WO 98/51 146). However, the activity of these mixtures is likewise not always satisfactory.

SUMMARY OF THE INVENTION

Compositions comprising a 5,7-dichloro-4-(4-fluoro-phenoxy)-quinoline of formula (I)

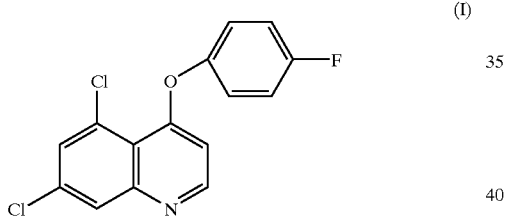

(I)

and at least one the compounds represented by formulae (II) to (IX) as given herein below are provided. The compositions have fungicidal activity.

DETAILED DESCRIPTION OF THE INVENTION

It has now been found that the novel active compound combinations comprising 5,7-dichloro-4-(4-fluoro-phenoxy)-quinoline of the formula

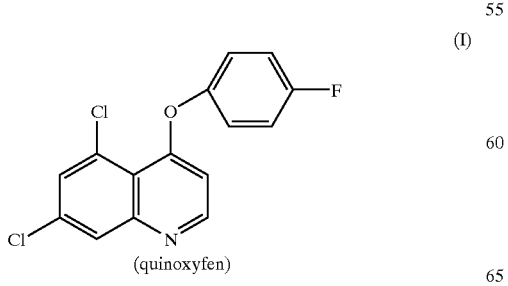

(I)

(quinoxyfen)

and (1) a triazole derivative of the formula

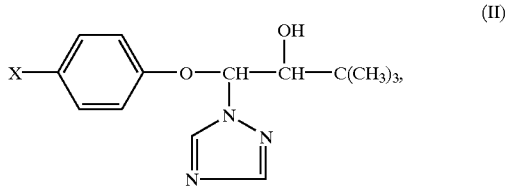

(II)

in which

X represents chlorine or phenyl, or (2) the N-dichloro-fluoro-methylthio-N',N'-dimethyl-N-p-tolylsulfamide of the formula

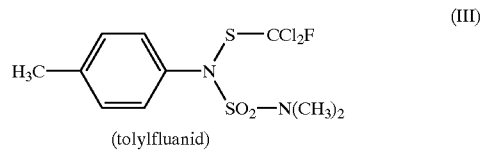

(III)

(tolylfluanid)

or (3) the zinc propylene-1,2-bis-(dithiocarbamidate) of the formula

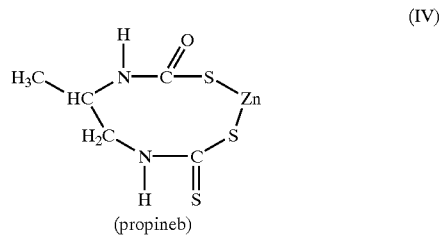

(IV)

(propineb)

or (4) the aniline derivative of the formula

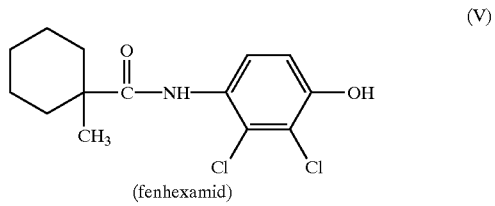

(V)

(fenhexamid)

or (5) the compound of the formula

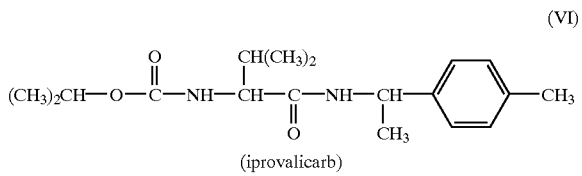

(VI)

(iprovalicarb)

or (6) the 2-[2-(1-chlorocyclopropyl)-3-(2-chlorophenyl)-2-hydroxypropyl]-2,4-dihydro-[1,2,4]-triazole-3-thione of the formula (VII)

or (7) the compound of the formula (VIII)

or (8) the benzimidazole derivative of the formula (IX)

have very good properties.

Surprisingly, the fungicidal activity of the active compound combinations according to the invention is considerably higher than the sum of the activities of the individual active compounds. Thus an unforeseeable, true synergistic effect is present, and not just an addition of activities.

The 5,7-dichloro-4-(4-fluoro-phenoxy)-quinoline of the formula (I) is known (cf. EP-A 0 326 330).

The formula (II) includes the compounds 1-(4-chloro-phenoxy)-3,3-dimethyl-1-(1,2,4-triazol-1-yl)-butan-2-ol of the formula (IIa)

(triadimenol)

and 1-(4-phenyl-phenoxy)-3,3-dimethyl-1-(1,2,4-triazol-1-yl)-butan-2-ol of the formula (IIb)

(bitertanol)

The 2-[2-(1-chlorocyclopropyl)-3-(2-chlorophenyl)-2-hydroxypropyl]-2,4-dihydro-[1,2,4]-triazole-3-thione can be present in the "thiono" form of the formula (VII)

or in the tautomeric "mercapto" form of the formula (VIIa)

For the sake of simplicity, only the "thiono" form is shown in each case.

The fungicidal components which are present in the active compound combinations according to the invention in addition to the 5,7-dichloro-4-(4-fluoro-phenoxy)-quinoline of the formula (I) are likewise known. Specifically, the active compounds are described in the following publications:

(1) Compounds of the formula (II)
DE-A 2 324 010
(2) Compound of the formula (III)
Pesticide Manual, 11$^{th}$ Edition, page 1208
(3) Compound of the formula (IV)
Pesticide Manual, 11$^{th}$ Edition, page 608
(4) Compound of the formula (V)
EP-A 0339418
(5) Compound of the formula (VI)
EP-A 0 472 996
(6) Compound of the formula (VII)
WO 96/16048
(7) Compound of the formula (VIII)
EP-A 0 882 043
(8) Compound of the formula (IX)
WO 97/06171

In addition to the active compound of the formula (I), the active compound combinations according to the invention comprise at least one active compound of the compounds from groups (1) to (8).

The synergistic effect is particularly pronounced when the active compounds in the active compound combinations according to the invention are present in certain weight ratios. However, the weight ratios of the active compounds in the active compound combinations can be varied within a relatively wide range. In general, from 0.1 to 10 parts by weight, preferably from 0.2 to 5 parts by weight, of active compound of group (1), from 1 to 50 parts by weight, preferably from 2 to 10 parts by weight, of active compound of group (2), from 1 to 50 parts by weight, preferably from 2 to 10 parts by weight, of active compound of group (3), from 0.1 to 10 parts by weight, preferably from 0.2 to 5 parts by weight, of active compound of group (4), from 0.1 to 10 parts by weight, preferably from 0.2 to 5 parts by weight, of active compound of group (5), from 0.1 to 10 parts by weight, preferably from 0.2 to 5 parts by weight, of active compound of group (6), from 0.05 to 10 parts by weight, preferably from 0.1 to 5 parts by weight, of active compound of group (7) and/or from 0.05 to 10 parts by weight, preferably from 0.1 to 5 parts by weight, of active compound of group (8)

are employed per part by weight of active compound of the formula (I).

The active compound combinations according to the invention have very good fungicidal properties and can be employed for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling cereal diseases, such as Erysiphe, Puccinia and Septoria, and for controlling diseases encountered in viticulture, such as Uncinula, Plasmopara and Botrytis, and furthermore in dicotyledonous crops for controlling powdery and downy mildew fungi and causative organisms of leaf spot.

The fact that the active compound combinations are well tolerated by plants at the concentrations required for controlling plant diseases permits the treatment of above-ground parts of plants, of propagation stock and seeds, and of the soil. The active compound combinations according to the invention can be employed for foliar application or else as seed dressings.

The active compound combinations according to the invention can be converted to the customary formulations, such as solutions, emulsions, suspensions, powders, foams, pastes, granules, aerosols, microencapsulations in polymeric substances and into coating compositions for seed, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Suitable liquid solvents include, essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose, and natural and synthetic polymers in the form of powders, granules or latices, such as gum arabic, polyvinyl alcohol and polyvinyl acetate, or else natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compounds, preferably between 0.5 and 90%.

In the formulations, the active compound combinations according to the invention can be present as a mixture with other known active compounds such as fungicides, insecticides, acaricides and herbicides, and as mixtures with fertilizers or plant growth regulators.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

When using the active compound combinations according to the invention, the application rates can be varied within a relatively wide range, depending on the kind of application. In the treatment of parts of plants, the application rates of active compound combination are generally between 0.1 and 10,000 g/ha, preferably between 10 and 1000 g/ha In the treatment of seed, the application rates of active compound combination are generally between 0.001 and 50 g per kilogram of seed, preferably between 0.01 and 10 g per kilogram of seed. In the treatment of the soil, the application rates of active compound combination are generally between 0.1 and 10,000 g/ha, preferably between 1 and 5000 g/ha.

The good fungicidal activity of the active compound combinations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated according to S. R. Colby ("Calculating Synergistic and Antagonistic Responses of Herbicide Combinations", Weeds 15, (1967), 20–22).

If

X is the efficacy when applying active compound A at an application rate of m g/ha, Y is the efficacy when applying active compound B at an application rate of n g/ha, and E is the efficacy when applying the active compounds A and B at application rates of m and n g/ha, then $$E = X + Y - \frac{X \cdot Y}{100}.$$

The efficacy is calculated in %. 0% is an efficacy which corresponds to that of the control, while an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The examples that follow illustrate the invention.

EXAMPLES

Example 1

Sphaerotheca Test (Cucumber)/Protective

Solvent: 47 parts by weight of acetone

Emulsifier: 3 parts by weight of alkyl-aryl polyglycol ether

To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the preparation of active compound at the stated application rate. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE 1

| | Sphaerotheca test (cucumber)/protective | |
|---|---|---|
| Active compound | Active compound application rate in g/ha | Efficacy in % |
| Known: | | |
| 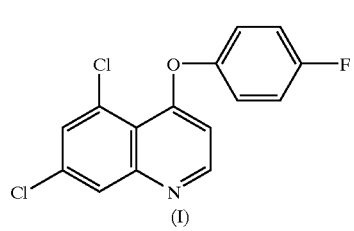 (I) | 10<br>5 | 63<br>57 |

TABLE 1-continued

Sphaerotheca test (cucumber)/protective

[Structure IIa: 4-chlorophenyl-O-CH(triazolyl)-CH(OH)-C(CH₃)₃] — 5 — 63

[Structure IIb: biphenyl-O-CH(triazolyl)-CH(OH)-C(CH₃)₃] — 10 — 27

[Structure III: 4-methylphenyl-N(S-CCl₂F)(SO₂-N(CH₃)₂)] — 50 — 0

[Structure IV: Zinc ethylene-bis-dithiocarbamate] — 50 — 0

[Structure V: 1-methylcyclohexyl-C(=O)-NH-(2,3-dichloro-4-hydroxyphenyl)] — 10 — 0

[Structure VI: (CH₃)₂CH-O-C(=O)-NH-CH(CH(CH₃)₂)-C(=O)-NH-CH(CH₃)-(4-methylphenyl)] — 10 — 0

| According to the invention: | | found | calc.*) |
|---|---|---|---|
| (I) + (IIa) 1:1 | 5 + 5 | 92 | 84 |
| (I) + (IIb) 1:1 | 10 + 10 | 95 | 73 |
| (I) + (III) 1:5 | 10 + 50 | 93 | 63 |
| (I) + (IV) 1:5 | 10 + 50 | 87 | 63 |
| (I) + | 10 + | 90 | 63 |

TABLE 1-continued

| Sphaerotheca test (cucumber)/protective | | |
|---|---|---|
| (V) 1:1 | 10 | |
| (I) + (VI) 1:1 | 10 + 10 | 90    63 |

*) found = efficacy found
calc. = efficacy calculated using Colby's formula

Example 2

Erysiphe Test (Barley)/Curative

Solvent: 10 parts by weight of N-methyl-pyrrolidone

Emulsifier: 0.6 parts by weight of alkylaryl polyglycol ether

To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for curative activity, young plants are dusted with spores of *Erysiphe graminis* f.sp. hordei. 48 hours after the inoculation, the plants are sprayed with the preparation of active compound at the stated application rate.

The plants are placed in a greenhouse at a temperature of approximately 20° C. and a relative atmospheric humidity of approximately 80%, to promote the development of mildew pustules.

Evaluation is carried out 7 days after the inoculation. 0% means an efficacy which corresponds to that of the control, whereas an efficacy of 100% means that no infection is observed.

Active compounds, application rates and tests results are shown in the table below.

TABLE 2

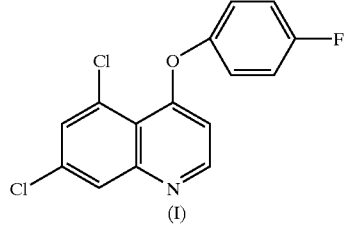

Erysiphe test (barley)/curative

| Active compound | Active compound application rate in g/ha | Efficacy in % |
|---|---|---|
| Known: | | |
| (I) | 25 | 57 |
| | 6.25 | 43 |
| (IIa) | 25 | 93 |
| According to the invention: | | |
| (I) + (IIa) 1:1 | 12.5 + 12.5 | 100 |
| (I) + (IIa) 1:3 | 6.25 + 18.75 | 100 |

Example 3

Phytophthora Test (Tomato)/Protective

Solvent: 47 parts by weight of acetone
Emulsifier: 3 parts by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration, or a commercial formulation of active compound or active compound combination is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at approximately 20° C. and 100% relative atmospheric humidity.

Evaluation is carried out 3 days after the inoculation. 0% means an efficacy which corresponds to that of the control, whereas an efficacy of 100% means that no infection is observed.

Active compounds, application rates and test results are shown in the table below.

What is claimed is:

1. A fungicidal composition comprising:

a 5,7-dichloro-4-(4-fluoro-phenoxy)-quinoline of the formula (I)

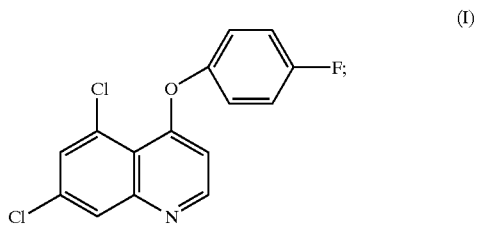

TABLE 3

| | Phytophthora test (tomato)/protective | |
|---|---|---|
| Active compound | Active compound application rate in g/ha | Efficacy in % |
| Known: | | |
| 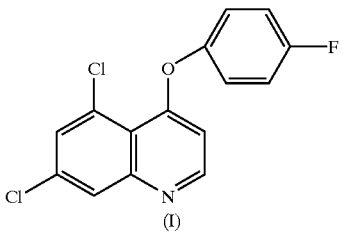 (I) | 5 | 4 |
| 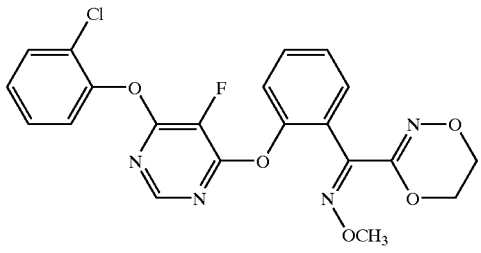 (VIII) | 5 | 45 |
| According to the invention: | | found  calc.*) |
| (I) + (VII) 1:1 | 5 + 5 | 65    47 |

*)found = efficacy found
calc. = efficacy calculated using Colby's formula and at least one of
a triazole of the formula (II)

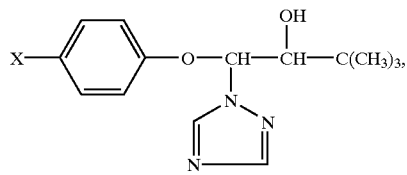

wherein

X represents chlorine or phenyl, a N-dichloro-fluoro-methylthio-N',N'-dimethyl-N-p-tolylsulfamide of the formula (III)

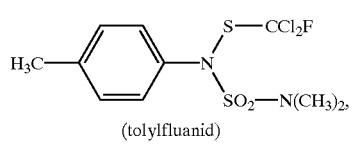

(tolylfluanid)

a zinc propylene-1,2-bis-(dithiocarbamidate) of the formula (IV)

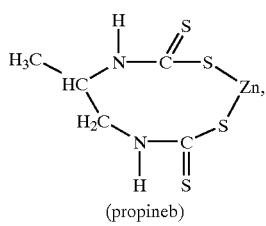

(propineb)

an aniline of the formula (V)

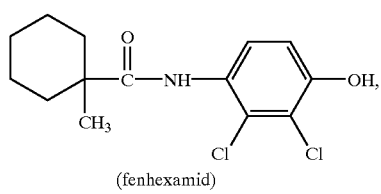

(fenhexamid)

a compound of the formula (VI)

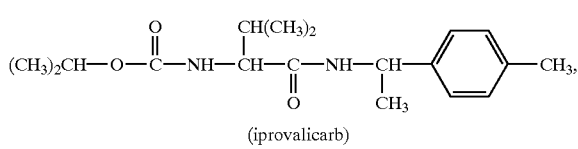

(iprovalicarb)

a 2-[2-(1-chlorocyclopropyl)-3-(2-chlorophenyl)-2-hydroxypropyl]-2,4-dihydro-[1,2,4]-triazole-3-thione of the formula (VII),

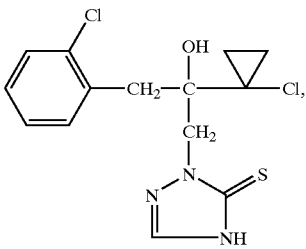

a compound of the formula (VIII)

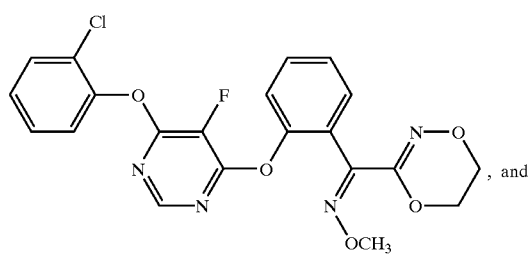
, and a benzimidazole of the formula (IX),

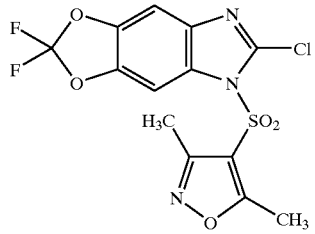

wherein the composition is synergistic.

2. The composition of claim 1, wherein the weight ratio of the compound of formula (I) to the compound of formula (II) is 1:0.1 to 1:10, the compound of formula (II) is 1:1 to 1:50, the compound of formula (IV) is 1:1 to 1:50, the compound of formula (V) is 1:0.1 to 1:10, the compound of formula (VI) is 1:0.1 to 1:10, the compound of formula (VII) is 1:0.1 to 1:10, the compound of formula (VIII) is 1:0.5 to 1:10 and the compound of formula (IX) is 1:0.5 to 1:10.

3. A method for controlling fungi, comprising applying the composition of claim 1 to said fungi and/or its locus.

4. A process for preparing a fungicidal composition comprising combining the composition of claim 1 and at least one of extender and surfactant.

5. The fungicidal composition of claim 1, wherein the weight ratio of the compound of formula (I) to the compound of formula (II) is 1:0.2 to 1:5, the compound of formula (III) is 1:2 to 1:10, the compound of formula (IV) is 1:2 to 1:10,
the compound of formula (V) is 1:0.2 to 1:5,
the compound of formula (VI) is 1:0.2 to 1:5,
the compound of formula (VII) is 1:0.2 to 1:5,
the compound of formula (VIII) is 1:0.5 to 1:5 and
the compound of formula (IX) is 1:0.5 to 1:5.

* * * * *